United States Patent
Wöhl et al.

(10) Patent No.: US 9,018,431 B2
(45) Date of Patent: Apr. 28, 2015

(54) CATALYST COMPOSITION AND PROCESS FOR OLIGOMERIZATION OF ETHYLENE

(75) Inventors: Anina Wöhl, Pullach (DE); Uwe Rosenthal, Lambrechtshagen (DE); Bernd H. Müller, Rostock (DE); Normen Peulecke, Rostock (DE); Stephan Peitz, Rostock (DE); Wolfgang Müller, Munich (DE); Heinz Bölt, Wolfrasthausen (DE); Andreas Meiswinkel, Munich (DE); Bhaskar Reddy Aluri, Rostock (DE); Mohammed Al-Hazmi, Riyadh (SA); Mohammed Al-Masned, Riyadh (SA); Khalid Al-Eidan, Riyadh (SA); Fuad Mosa, Riyadh (SA)

(73) Assignees: Saudi Basic Industries Corporation, Riyadh (SA); Linde AG (DE)

(*) Notice: Subject to any disclaimer, the term of this patent is extended or adjusted under 35 U.S.C. 154(b) by 819 days.

(21) Appl. No.: 13/263,113

(22) PCT Filed: Mar. 24, 2010

(86) PCT No.: PCT/EP2010/001842
§ 371 (c)(1),
(2), (4) Date: Oct. 6, 2011

(87) PCT Pub. No.: WO2010/115520
PCT Pub. Date: Oct. 14, 2010

(65) Prior Publication Data
US 2012/0029258 A1 Feb. 2, 2012

(30) Foreign Application Priority Data
Apr. 9, 2009 (EP) .................................. 09005212

(51) Int. Cl.
*C07C 2/02* (2006.01)
*B01J 31/00* (2006.01)
(Continued)

(52) U.S. Cl.
CPC .............. *B01J 31/189* (2013.01); *B01J 31/143* (2013.01); *B01J 2231/20* (2013.01);
(Continued)

(58) Field of Classification Search
CPC .................. B01J 2531/0255; B01J 2531/0258
USPC ......... 502/208, 210, 103, 117, 118, 119, 121, 502/123, 128; 585/510, 511, 512, 513, 520, 585/521, 522, 523
See application file for complete search history.

(56) References Cited

U.S. PATENT DOCUMENTS 5,104,840 A * 4/1992 Chauvin et al. ............... 502/117
6,018,016 A    1/2000 Dossett
(Continued)

FOREIGN PATENT DOCUMENTS

CN    1490290 A      4/2004
EP    2239056 B1    10/2010
(Continued)

OTHER PUBLICATIONS

Bent, E. G.; Schaeffer, R.; Haltiwanger, R. C.; Norman, A. D. "Synthesis of Mono- and Diphosphorous Phosphazane Oligomer/Polymer Precursors", Inorg. Chem. 1990, 29, 2608-2613.*
(Continued)

*Primary Examiner* — In Suk Bullock
*Assistant Examiner* — Aaron Pierpont
(74) *Attorney, Agent, or Firm* — Cantor Colburn LLP

(57) ABSTRACT

The present invention relates to a catalyst composition for oligomerization of ethylene, comprising a chromium compound; a ligand of the general structure $R_1R_2P-N(R_3)-P(R_4)-N(R_5)-H$, wherein $R_1, R_2, R_3, R_4$ and $R_5$ are independently selected from halogen, amino, trimethylsilyl, $C_1-C_{10}$-alkyl, aryl and substituted aryl; a modifier containing organic or inorganic halide; and an activator or co-catalyst; and a process for oligomerization utilizing that catalyst.

20 Claims, 4 Drawing Sheets

Figure 1:
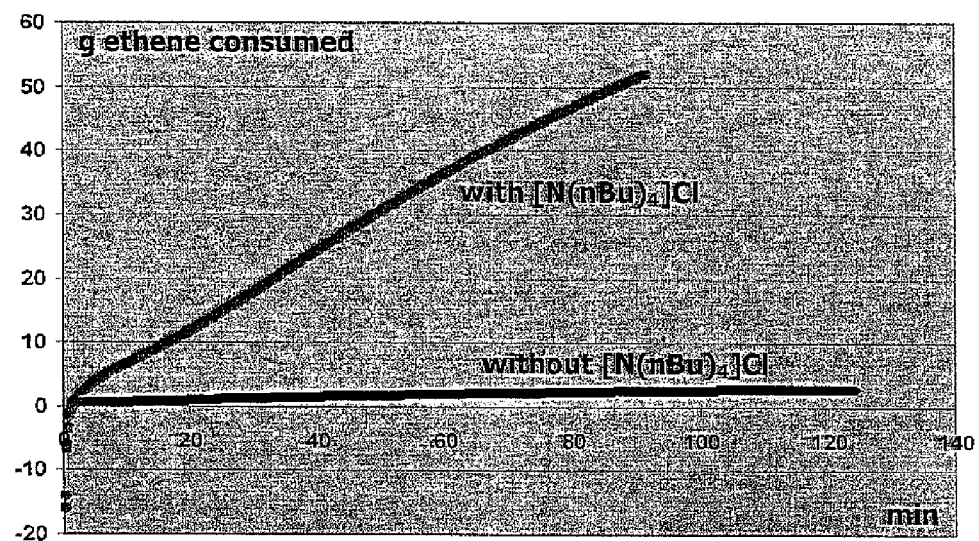

(51) Int. Cl.
  B01J 37/00 (2006.01)
  C08F 4/02 (2006.01)
  C08F 4/60 (2006.01)
  B01J 31/18 (2006.01)
  B01J 31/14 (2006.01)
  C07C 2/36 (2006.01)

(52) U.S. Cl.
  CPC ...... B01J 2531/0258 (2013.01); B01J 2531/62 (2013.01); C07C 2/36 (2013.01); C07C 2531/14 (2013.01); C07C 2531/24 (2013.01)

(56) References Cited

U.S. PATENT DOCUMENTS

| | | | |
|---|---|---|---|
| 6,133,495 A * | 10/2000 | Urata et al. | 585/513 |
| 6,800,702 B2 | 10/2004 | Wass | |
| 7,022,788 B2 | 4/2006 | Wass | |
| 2006/0153615 A1 | 7/2006 | Kamei | |
| 2007/0185357 A1 | 8/2007 | DeBoer et al. | |
| 2007/0232481 A1 * | 10/2007 | Zhang et al. | 502/104 |

FOREIGN PATENT DOCUMENTS

| | | |
|---|---|---|
| EP | 1456152 B1 | 6/2012 |
| EP | 1456153 B1 | 6/2012 |
| WO | 03053891 A1 | 7/2003 |
| WO | 2004056479 A1 | 7/2004 |
| WO | 2004056578 A1 | 7/2004 |
| WO | 2005039758 A1 | 5/2005 |
| WO | WO 2009/006979 A1 | 1/2009 |
| WO | WO 2009/068157 A1 | 6/2009 |

OTHER PUBLICATIONS

"Inorganic Reactions and Methods", vol. 7; J.J. Zuckerman, Ed.; VCH: New York, NY, 1988; p. 46.*
CN1490290A; machine translation.
Agapie, Theodor, et al., "A Chromium-Diphosphine System for Catalytic Ethylene Trimerization: Synthetic and Structural Studies of Chromium Complexes with a Nitrogen-Bridged Diphosphine Ligand with ortho-Methoxyaryl Substituents", Organometallics 2006, 25, 2733-2742.
Agapie, Theodor, et al, "Mechanistic Studies of the Ethylene Trimerization Reaction with Chromium-Diphosphine Catalysts: Experimental Evidence for a Mechanism Involving Metallacyclic Intermediates", J. Am. Chem. Soc. 2004, 126, 1304-1305.
Blann, Kevin, et al., "Highly selective chromium-based ethylene trimerisation catalysts with bulky diphosphino-amine ligands", Chem. Comm., 2005, 620-621.
Dixon et al.; "Advances in Selective Ethylene Trimerisation—A Critical Overview"; Journal of Organometallic Chemistry; vol. 689; 2004; pp. 3641-3668.
Elowe, Paul R. et al., "Nitorgen-Linked Diphosphine Ligands with Ethers Attached to Nitrogen for Chromium-Catalyzed Ethylene Tri- and Tetramerization", Organometallics 2006, 25, 5255-5260.
European Search Report for EP09005212 mailed Jun. 17, 2009, 6 pages.
Hagen, Henk et al., "Selective ethylene trimerization: A study into the mechanism and the reduction of PE formation", Journal of Molecular Catalysis A: Chemical 248 (2006) 237-247.
Jabri, Amir. et al., "Role of the Metal Oxidation State in the SNS-Cr Catalyst for Ethylene Trimerization: Isolation of Di- and Trivalent Cationic Intermediates", J. Am. Chem. Soc. 2006, 128, 9238-9247.
Jabri, Amir. et al., "Isolation of Cationic Chromium (II) Species in a Catalytic System for Ethylene Tri-and Tetramerization", Organometallics 2006, 25, 715-718.
Kuhlmann, Sven, et al., "Chromium catalyzed tetramerization of ethylene in a continuous tube reactor, Proof of concept and kinetic aspects", Journal of Catalysis 2009, 262, 83-91.
McGuinness, David S. et al., "Ethylene Trimerization with Cr-PNP and Cr-SNS Complexes: Effect of Ligand Structure, Metal Oxidation State, and Role of Activator on Catalysis", Organometallics 2006, 25, 3605-3610.
McGuinness, David S., et al., "Novel Cr-PNP complexes as catalysts for the trimerization of ethylene", Chem. Commun., 2003, 334-335.
Overett, Matthew J. et al, "Ethylene trimerisation and tetramerisation catalysts with polor-substituted diphosphinoamine ligands", Chem. Commun., 2005, 622-624.
International Search Report; International Application No. PCT/EP2010/001842; International Filing Date: Mar. 24, 2010; Date of Mailing: May 4, 2010; 3 Pages.
Written Opinion of the International Searching Authority; International Application No. PCT/EP2010/001842; International Filing Date: Mar. 24, 2010; Date of Mailing: May 4, 2010; 5 Pages.
Schofer, Susan J. et al., "Ethylene Trimerization Catalysts Based on Chromium Complexes with a Nitrogen-Bridged Diphosphine Ligand Having ortho-Methoxyaryl or ortho-Thiomethoxy Substituents: Well-Defined Catalyst Precursors and Investigations of the Mechanism", Organometallics 2006, 25, 2743-2749.
Temple, Claire, et al., "The Question of the Cr-Oxidation State in the {Cr(SNS)} Catalyst for Selective Ethylene Trimerization: An Unanticipated Re-Oxidation Pathway", Angew. Chem. Int. Ed. 2006, 45, 7050-7053.

* cited by examiner

CATALYST COMPOSITION AND PROCESS FOR OLIGOMERIZATION OF ETHYLENE

Existing processes for the production of linear alpha olefins (LAOs), including comonomer-grade 1-hexene and 1-octene, rely on the oligomerization of ethylene. These processes have in common that they lead to a product distribution of ethylene-oligomers of chain length 4, 6, 8 and so on. This is due to a chemical mechanism which is widely governed by competing chain growth- and displacement reaction steps, leading to a Schulz-Flory- or Poisson-product distribution.

From the marketing point of view, this product distribution poses a formidable challenge for the full-range alpha olefins producer. The reason is that each market segment served exhibits a very different behavior in terms of market size and growth, geography, fragmentation etc. It is, therefore, very difficult for the producer to adapt to the market requirements since part of the product spectrum might be in high demand in a given economic context, while at the same time other product cuts might not be marketable at all or only in a marginal niche. Currently, the highest-value LAO product is comonomer-grade 1-hexene for the polymer industry.

Thus, the on-purpose production of the most economically viable LAOs, i.e. comonomer-grade 1-hexene, appears highly desirable. To meet the requirements regarding high C6-selectivities, new processes have been developed. A selective C6-commercial process has been commissioned by Chevron Phillips, see for a comprehensive review J. T. Dixon, M. J. Green, F. M. Hess, D. H. Morgan, "Advances in selective ethylene trimerisation—a critical overview", Journal of Organometallic Chemistry 689 (2004) 3641-3668.

Furthermore, WO 03/053891 A1, discloses chromium-based selective ethylene-trimerization catalyst systems, typically of the type $CrCl_3$(bis-(2-diphenylphosphino-ethyl)amine)/MAO (methylaluminoxane). Also disclosed were variations of the ligand structure (e.g. bis(2-diethylphosphino-ethyl)-amine, pentamethyldiethylenetriamine etc.). However, all these complexes generate considerable amounts of unwanted side products such as LAOs other than 1-hexene, as well as waxes and polyethylene.

A large body of scientific publications and patent literature describes the use of chromium-based metal-organic complexes with ligands featuring the basic PNP-structure (for example bis(diphenylphosphino)amine-ligands), see D. S. McGuinness, P. Wasserscheid, W. Keim, C. Hu, U. Englert, J. T. Dixon, C. Grove, "Novel Cr—PNP complexes as catalysts for the trimerization of ethylene", Chem. Commun., 2003, 334-335; K. Blann, A. Bollmann, J. T. Dixon, F. M. Hess, E. Killian, H. Maumela, D. H. Morgan, A. Neveling, S. Otto, M. J. Overett, "Highly selective chromium-based ethylene trimerisation catalysts with bulky diphosphinoamine ligands", Chem. Comm., 2005, 620-621; M. J. Overett, K. Blann, A. Bollmann, J. T. Dixon, F. Hess, E. Killian, H. Maumela, D. H. Morgan, A. Neveling, S. Otto, "Ethylene trimerisation and tetramerisation catalysts with polar-substituted diphosphinoamine ligands", Chem. Commun., 2005, 622-624; D. S. McGuinness, D. B. Brown, R. P. Tooze, F. M. Hess, J. T. Dixon, A. M. Z. Slavin, "Ethylene Trimerization with Cr—PNP and Cr—SNS Complexes: Effect of Ligand Structure, Metal Oxidation State, and Role of Activator on Catalysis", Organometallics 2006, 25, 3605-3610; A. Jabri, P. Crewdson, S. Gambarotta, I. Korobkov, R. Duchateau, "Isolation of a Cationic Chromium(II) Species in a Catalytic System for Ethylene Tri- and Tetramerization", Organometallics 2006, 25, 715-718; T. Agapie, S. J. Schofer, J. A. Labinger, J. E. Bercaw, "Mechanistic Studies of the Ethylene Trimerization Reaction with Chromium-Diphosphine Catalysts: Experimental Evidence for a Mechanism Involving Metallacyclic Intermediates", J. Am. Chem. Soc. 2004, 126, 1304-1305; S. J. Schofer, M. D. Day, L. M. Henling, J. A. Labinger, J. E. Bercaw, "Ethylene Trimerization Catalysts Based on Chromium Complexes with a Nitrogen-Bridged Diphosphine Ligand Having ortho-Methoxyaryl or ortho-Thiomethoxy Substituents: Well-Defined Catalyst Precursors and Investigations of the Mechanism", Organometallics 2006, 25, 2743-2749; S. J. Schofer, M. D. Day, L. M. Henling, J. A. Labinger, J. E. Bercaw, "A Chromium-Diphosphine System for Catalytic Ethylene Trimerization: Synthetic and Structural Studies of Chromium Complexes with a Nitrogen-Bridged Diphosphine Ligand with ortho-Methoxyaryl Substituents", Organometallics 2006, 25, 2733-2742; P. R. Elowe, C. McCann, P. G. Pringle, S. K. Spitzmesser, J. E. Bercaw, "Nitrogen-Linked Diphosphine Ligands with Ethers Attached to Nitrogen for Chromium-Catalyzed Ethylene Tri- and Tetramerization", Organometallics 2006, 25, 5255-5260; Sasol patent applications WO 2004/056578, WO 2004/056479, EP 02 794 480.0, EP 02 794 479.2; S. Kuhlmann, C. Paetz, C. Haegele, K. Blann, R. Walsh, J. T. Dixon, J. Scholz, M. Haumann, P. Wasserscheid, "Chromium catalyzed tetramerization of ethylene in a continuous tube reactor—Proof of concept and kinetic aspects", J. Catal. 2009, 262, 83-91 or the SNS-structure D. S. McGuinness, D. B. Brown, R. P. Tooze, F. M. Hess, J. T. Dixon, A. M. Z. Slavin, "Ethylene Trimerization with Cr-PNP and Cr-SNS Complexes: Effect of Ligand Structure, Metal Oxidation State, and Role of Activator on Catalysis", Organometallics 2006, 25, 3605-3610; A. Jabri, C. Temple, P. Crewdson, S. Gambarotta, I. Korobkov, R. Duchateau, "Role of the Metal Oxidation State in the SNS-Cr Catalyst for Ethylene Trimerization: Isolation of Di- and Trivalent Cationic Intermediates, J. Am. Chem. Soc. 2006, 128, 9238-9247; C. Temple, A. Jabri, P. Crewdson, S. Gambarotta, I. Korobkov, R. Duchateau, "The Question of the Cr-Oxidation State in the {Cr(SNS)} Catalyst for Selective Ethylene Trimerization: An Unanticipated Re-Oxidation Pathway", Angew. Chem. Int. Ed. 2006, 45, 7050-7053 for both, trimerization and tetramerization of ethylene.

Excess amounts of MAO are most commonly used as activator/co-catalyst. This becomes especially evident in the recent kinetic study of S. Kuhlmann, C. Paetz, C. Haegele, K. Blann, R. Walsh, J. T. Dixon, J. Scholz, M. Haumann, P. Wasserscheid, "Chromium catalyzed tetramerization of ethylene in a continuous tube reactor—Proof of concept and kinetic aspects", J. Catal. 2009, 262, 83-91, where an Al- (in the form of MAO or modified MAO) to Cr-ratio of up to 8100 mol/mol was employed. While the required amounts of the chromium-precursor (e.g. chromium acetylacetonate) are impressively low, due to the very high catalyst activities reported in these studies, this alleged advantage turns out to be eventually detrimental: very low concentrations of the catalyst's active component render the system extremely susceptible to minute traces of inhibitors and catalyst poisons that are inherently inevitable in a technical environment. These can be impurities in feedstock, solvent or auxiliary additives (e.g. water, oxygen, sulfur compounds, corrosion products, etc.). To avoid poisoning or deactivation, excess amounts of a scavenger are required, for example MAO. Thus, seemingly low costs for the catalyst's active component are being overcompensated by the cost for huge amounts of scavenger/co-catalyst/activator.

While the majority of the published studies rely on Cr—PNP complexes, some deal with other ligands, e.g. of the general formula (R1)(R2)P—X—P(R3)(R4), where X is a bivalent organic bridging group, see WO 2005/039758 A1, "Catalytic Trimerization of Olefinic Monomers", or deal with entirely different complexes, such as titanocenes, see H. Hagen, W. P. Kretschmer, F. R. van Buren, B. Hessen, D. A. van Oeffelen, "Selective ethylene trimerization: A study into the mechanism and the reduction of PE formation", Journal of Molecular Catalysis A: Chemical 248 (2006) 237-247. In either case, the major concern is always selectivity and minimization of polyethylene formation.

The most advanced approach to the problem was recently disclosed in WO 2009/006979 A2, where a catalyst system for the selective trimerization of ethylene was described. This catalyst system comprises a chromium source, a ligand featuring a "PNPNH-backbone" and a co-catalyst/activator. In a typical embodiment, the chromium source is $CrCl_3(THF)_3$ (THF=tetrahydrofurane), the PNPNH-ligand is $(Ph)_2P$—N(i-Pr)-P(Ph)-N(i-Pr)-H (Ph=phenyl group, i-Pr=isopropyl group) and the co-catalyst is triethylaluminum (TEA). Using this catalyst system for the ethylene-trimerization, C6-yields in excess of 90 wt % were achieved with 1-hexene selectivities in the C6-fraction of more than 99.5 wt %. Lower process temperatures, i.e. 40-50° C., lead to very high 1-hexene selectivities and yields, whereas higher temperatures (65-90° C.) favor the formation of small amounts of C4-olefins as main byproducts. Also, the catalytic activity decreases to some extent as the process temperature increases while, simultaneously, the 1-hexene selectivity remains exceptionally high.

While the catalyst system from WO 2009/006979 A2 works very well at low process temperatures (e.g. 40-50° C.) and these mild conditions might be advantageous in some technical environments, it might still be desirable to operate the process at higher temperatures in other cases.

Higher temperatures would allow to utilize the enthalpy of evaporation of the solvent, or of suitable solvent constituents, for cooling the reaction mass in the exothermic ethylene-trimerization reaction. This cooling effect is especially useful since the incorporation of heat exchanger surfaces in close contact with the reaction mass is less advantageous in these processes, due to the fact that these surfaces are prone to fouling effects, caused by wax- or polymer-formation under upset conditions.

The selective ethylene trimerization catalysts and processes disclosed so far in scientific- and patent-literature generally have to cope with the following challenges:

Low selectivities to the desired product 1-hexene (undesired by-products from side reaction channels).

Limited purities of the products, i.e. the selectivities within the C6-cut (isomerization, branched olefin formation etc.).

Wax formation, i.e. formation of heavy, long-chain, high carbon-number products.

Polymer formation (polyethylene, branched and/or cross-linked PE); this leads to considerable product yield loss and fouling of equipment.

Poor turnover rates/catalyst activity, resulting in high cost per kg product.

High catalyst- or ligand cost.

Difficult ligand synthesis, resulting in poor availability and high catalyst cost.

Susceptibility of catalyst performance, in terms of both activity and selectivity, to trace impurities (catalyst losses/-poisoning).

Difficult handling of catalyst components in a technical environment (catalyst complex synthesis, pre-mixing, inertization, catalyst- or ligand-recovery).

Harsh reaction conditions, i.e. high temperatures and pressures, resulting in high invest-, maintenance-, and energy-cost.

High co-catalyst/activator cost and/or -consumption.

Susceptibility to varying co-catalyst qualities; often the case when larger amounts of relatively ill-defined compounds must be used as activators (e.g. certain MAO-varieties).

Very narrow or unsuitable window of operability of the catalyst system in terms of process conditions, such as temperature, pressure, residence time, catalyst concentration and the like.

It is an object of the invention to provide a catalyst composition and a process for oligomerization of ethylene overcoming the disadvantages of the prior art and to create an entirely new ethylene trimerization catalyst system of unprecedented selectivity and sufficiently high activity/turn-over-frequency for a technical process. Furthermore, the invention aims at an enhancement of the catalyst system's flexibility in terms of boundary conditions imposed by chemical engineering considerations.

The first object is achieved by a catalyst composition comprising:

(a) a chromium compound;
(b) a ligand of the general structure $R_1R_2P$—$N(R_3)$—P$(R_4)$—$N(R_5)$—H,
wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, aryl and substituted aryl, or any cyclic derivative of the ligand, wherein at least one of the P or N atoms of the PNPNH-unit can be also a member of a ring system, the ring system being formed from one or more constituent compounds of the ligand by substitution;
(c) a modifier containing organic or inorganic halide; and
(d) an activator or co-catalyst.

As it is to be understood, any cyclic derivative of the ligand can be utilized, wherein at least one of the P or N atoms of the PNPNH-unit is a ring member, the ring being formed from one or more constituent compounds of the ligand by substitution, i.e. by formally eliminating per constituent compound either two whole groups $R_1$-$R_5$ (as defined) or H, one atom from each of two groups $R_1$-$R_5$ (as defined) or a whole group $R_1$-$R_5$ (as defined) or H and an atom from another group $R_1$-$R_5$ (as defined), and joining the formally so-created valence-unsaturated sites by one covalent bond per constituent compound to provide the same valence as initially present at a given site.

Preferably the chromium compound is selected from organic or inorganic salts, coordination complexes and organometallic complexes of Cr(II) or Cr(III), preferably $CrCl_3$ $(THF)_3$, Cr(III) acetyl acetonate, Cr(III) octanoate, chromium hexacarbonyl, Cr(III)-2-ethylhexanoate, benzene (tricarbonyl)-chromium or Cr(III)chloride.

If a halogen containing chromium compound is selected, such a compound cannot act both as chromium compound and a modifier containing a halide as such a compound can only provide an intramolecular interaction, whereas a modifier is intended to provide an intermolecular interaction. Thus, chromium compound and modifier have to be different compounds.

Even preferred the modifier is selected from ammonium or phosphonium salts of the type $[H_4E]X$, $[H_3ER]X$, $[H_2ER_2]X$, $[HER_3]X$ or $[ER_4]X$ with E=N or P, X=Cl, Br or I and R=alkyl, cycloalkyl, acyl, aryl, alkenyl, alkynyl or the corresponding bridging di-, tri- or multiunits; HX; or RX; preferably tetraphenyl phosphoniumchloride, tetraethylammoniumchloride-monohydrate, tetraethylammoniumchloride, isopropylamine-hydrochloride, triethylamine-hydrochloride, tetrapropylammonium chloride, tetra-n-butylammonium chloride, tetraethylammonium bromide, p-toluidinehydrochloride, dimethyldistearylammonium chloride, (tri-n-butyl)-n-tetradecylphosphonium chloride, benzoyl chloride and acetyl chloride.

In general, any compound which can release a halogenide is a suitable modifier.

The modifier may be also selected from ammonium or phosphonium salts based on non-cyclic and cyclic amines, like piperidine. The term "bridging di-, tri- or multi units" is to be understood to comprise, e.g., N,N,N',N'-tetramethylethylenediamine or ethylenebis(diphenyl-phosphin), as well as, for tri- or multiunits, compounds according to the type $Y(HER)_n$ and $Y(ER_2)_n$ with E=N or P, n≥2 and Y=any unit (branched alkyl, cycloalkyl, aryl, etc.) which bridges the substituents -EHR or -$ER_2$.

In other words, combining the chromium source and the modifier may result in ammonium- and phosphonium-chromate complexes of the type $[A][CrX_4]$, $[A]_2[CrX_5]$ and $[A]_3$-$[CrX_6]$ with $[A]=[H_4E]^+$, $[H_3ER]^+$, $[H_2ER_2]^+$, $[HER_3]^+$, $[ER_4]^+$, with E, X and R as defined above.

Also, combining the chromium source and the modifier may result in mixtures from the components:
Cr-salts and $[H_4E]X$, $[H_3ER]X$, $[H_2ER_2]X$, $[HER_3]X$, $[ER_4]X$,
Cr-salts and anhydrous hydrohalogen acid, especially hydrochloric acid, with $H_3E$, $H_2ER$, $HER_2$ or $R_3E$,
Cr-salts and RX, for example benzoyl chloride, with $H_3E$, $H_2ER$, $HER_2$ or $R_3E$.

In an alternative, the invention provides a catalyst composition comprising:
(a') a halide containing chromium compound;
(b) a ligand of the general structure $R_1R_2P$—$N(R_3)$—P$(R_4)$—$N(R_5)$—H,
wherein $R_1$, $R_2$, $R_3$, $R_4$ and $R_5$ are independently selected from halogen, amino, trimethylsilyl, $C_1$-$C_{10}$ alkyl, aryl and substituted aryl;
(c') a modifier containing a free amine group; and
(d) an activator or co-catalyst.

Preferably the modifier containing a free amine group is selected from primary, secondary or tertiary aliphatic or aromatic amine. A preferred aliphatic amine is isopropylamine.

The activator or co-catalyst is selected from trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane (MAO) or mixtures thereof.

In one embodiment the molar ligand/Cr ratio is from 0.5:1 to 50:1, preferably 0.8:1 to 2.0:1.

The molar Al/Cr ratio is preferably from 1:1 to 1000:1, more preferably 10:1 to 200:1.

The molar modifier/Cr ratio is preferably from 0.01:1 to 100:1, more preferably 1:1 to 20:1.

In a further embodiment the molar ratio of Cr/halide is from 1:1 and 1:20.

As it is obvious for someone skilled in the art, the components for providing the catalyst composition are more or less considered as starting materials, but may be converted when the components are mixed to form the catalyst composition. In this regard, the catalyst composition according to the present invention can be also illustrated as being containable by combining at least components (a), (b), (c) and (d) according the first embodiment, and combining at least components (a'), (b), (c') and (d) according to the second embodiment.

The second object is achieved by a process for oligomerization of ethylene, comprising subjecting a catalyst composition according to the invention to a gas phase of ethylene in a reactor and conducting an oligomerization.

Preferably the oligomerization is carried out at a pressure of 1 to 200 bar, preferably 10 to 50 bar.

Also preferred the oligomerization is carried out at a temperature of from 10 to 200° C., preferably 20 to 100° C.

Finally the mean residence time is preferably from 10 minutes to 20 hours, preferably 1 to 4 hours.

Surprisingly, it was found in a first embodiment that modifiers that introduce an organic or inorganic halide into the catalyst system, are capable to enhance the overall performance of catalyst compositions to a great extent. This is probably accomplished by the formation of entirely new catalytic centers via the reaction of the Cr-/PNPNH-ligand/activator—catalysts with the halide—bearing modifiers.

In an alternative embodiment of the invention, a halide-containing chromium source, for example $CrCl_3(THF)_3$ or $CrCl_3$, can be combined with a free amine, preferentially an aliphatic amine, e.g. isopropylamine. This combination constitutes an "in-situ" alkyl ammonium chloride component and is therefore roughly equivalent to a catalyst composition of the first embodiment.

Besides enhancing the window of operability in terms of process conditions, the invention also provides more flexibility regarding the catalyst system's activity, thus affecting process productivity as desired. While maintaining very high levels of 1-hexene selectivity, process productivity can be enhanced whenever the heat removal- and mixing rates in the technical process allow to do so. Conversely, if heat removal is critical, the catalytic system's overall activity can be adjusted so as to avoid potential runaway conditions.

Prior art processes do so by simply lowering total catalyst concentrations to extremely low levels. This, however, requires the addition of copious amounts of co-catalyst/activator (e.g. MAO), since the activator also acts as a scavenger for trace amounts of catalyst poisons or deactivating impurities, that are almost inevitably abundant in real technical processes.

The invention avoids these tradeoffs and restrictions by providing a wide range of flexibility in terms of catalyst composition which, in turn, controls process productivity, heat release and selectivity on any desired process temperature level within the scope defined by the system's chemical properties. This flexibility is achieved on catalyst concentration levels that can easily be handled and controlled in a technical environment.

The active catalyst is prepared by combining the chromium source and the ligand in a suitable solvent, preferentially toluene, 1-hexene or cyclohexane, such that the chromium concentration is 0.001 to 100 mmol/l, preferentially between 0.1 and 10 mmol/l and the ligand/Cr-ratio is 0.5:1 to 50:1 mol/mol, preferentially between 0.8:1 to 2:0:1 mol/mol. An example for a preferred structure of the ligand is shown below and is henceforth referred to as the PNPNH-ligand.

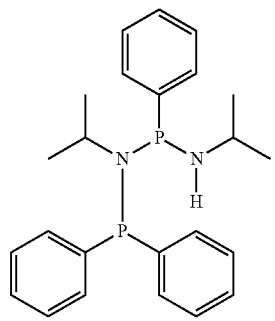 [SMILES: CC(C)NP(c1ccccc1)N(C(C)C)P(c1ccccc1)c1ccccc1]

The co-catalyst, preferentially triethylaluminum or any mixture of triethylaluminum and MAO, is added as a solution in toluene, so as to result in an Al/Cr-ratio between 1:1 and 1:1000 mol/mol. The preferred Al/Cr-ratio is 10:1 to 200:1 mol/mol.

The modifier is added so as to result in a modifier/Cr-ratio of 0.01:1 to 100:1 mol/mol, preferentially 1 to 20 mol/mol.

The solvent toluene can be replaced by other solvents or mixtures of solvents such as aromatic hydrocarbons other than toluene (benzene, ethylbenzene, cumenene, xylenes, mesitylene etc.), aliphatic hydrocarbons (both straight-chain and cyclic, e.g. hexane, octane, cyclohexane), straight-chain olefins like hexene, heptene, octene etc. or ethers like, for example, diethylether or tetrahydrofurane. Most preferred is 1-hexene, because this is also the product of the process and using it as a solvent is advantageous because this greatly simplifies the separation units of the process. Furthermore, the solubility of ethene in 1-hexene is even better than in toluene.

The catalyst solution is then subjected to a gas phase of dry ethene at pressures between 1 and 200 bar, preferentially 10 and 80 bar in a suitable pressure reactor. The reactor can be of any type suitable to provide sufficient contact between gas- and liquid phase, such as bubble column reactors, stirred tank reactors, flow reactors with fixed or distributed ethylene-injection and the like. The main task of the selected reactor configuration is to ensure a sufficiently fast gas-to liquid mass transfer, so as to avoid phase transfer limitations, especially at high conversion rates achieved by highly active catalyst compositions.

Preferred reaction temperatures are between 10 and 200° C., the most preferred temperature regime is 20 to 100° C. Mean residence times and residence time distributions (in case of a continuous process) are chosen so as to achieve sufficient conversion at high selectivities. Typical mean residence times are between 10 minutes and 20 hours (depending on temperature and pressure). The preferred range is 1 to 4 hours.

To summarize, the present invention provides the following advantages: production of 1-hexene with high turnover rate and selectivity; high reproducibility, i.e. catalyst system is stable against interference from impurities and fluctuations in process conditions; selective production of 1-hexene; no undesired by-products; expensive co-catalysts such as MAO are totally or to a large extent replaced by cheaper substances, preferably by triethyl aluminum; co-catalysts prone to quality instabilities, due to their relatively pure definition of chemical structure (MAO), are partly or totally replaced by well-defined chemical species (trietyl aluminum); no wide LAO product distribution; very good suppression of polymer formation; mild reaction conditions, consequently low invest costs for technical-scale plant and low energy and operation costs; allows for relatively simple, straight forward process design; very high C6-selectivities lead to high product purities without additional purification steps in the separation train; readily available, cheap chromium sources; catalyst system can easily be fine tuned so as to meet the boundary conditions defined by the technical environment; wide variability of possible operating conditions; easy optimisation of activity and selectivity according to variable needs; and simple and cheap catalyst preparation.

The present invention aims primarily at the improvement of the catalyst's activity, while, simultaneously, maintaining the high selectivities/yields as known in the prior art. Further, it was, preferably, found that the behaviour of many of the Cr precursors which are readily available and cheap, can be improved when adding the modifier. This is especially true for $Cr(acac)_3$. Using $Cr(acac)_3$ with the ligand forms a real physical solution (no concentration gradients) of a virtually unlimited shelf-life time.

Further advantages and features of the present invention are now illustrated in the following example section with reference to the accompanying drawings wherein FIGS. 1-7 illustrate the ethylene consumption with time for experiments according to examples 3 to 9.

EXAMPLE 1

Ethylene Trimerization Using the $CrCl_3(THF)_3$/PN-PNH/TEA/$[PPh_4]Cl$ and $[NEt_4]Cl.H_2O$-Catalyst System A 300 ml pressure reactor, equipped with dip tube, thermowell, gas entrainment stirrer, cooling coil, control units for temperature, pressure, and stirrer speed (all hooked up to a data acquisition system) was inertized with dry argon. The isobaric ethene supply was maintained by an aluminum pressurized gas cylinder on a balance to monitor the ethene consumption over time by means of a computerized data acquisition system.

Before conducting an experiment, the reactor was heated to 100° C. at reduced pressure for several hours to eliminate traces of water, oxygen and oxygenated impurities.

For the catalyst preparation, the suitable amounts of the PNPNH-ligand (61.4 mg $(Ph)_2P$—$N(iPr)$-$P(Ph)$-$N(iPr)$-H, Ph=phenyl, iPr=isopropyl), chromium precursor ($CrCl_3(THF)_3$, 37.5 mg) and the modifier tetraphenylphosphonium-chloride ($P(Ph)_4Cl$, 37.7 mg) were weighed in and charged to a Schlenk tube under inert atmosphere. A volume of 100 ml anhydrous toluene was added and the solution was stirred by means of a magnetic stirrer. After dissolving the Cr-compound and ligand, the required amount of a 1.9 mol/l solution of TEA in toluene (3.7 ml) was added. The solution was immediately transferred to the reactor and the reaction was started.

The chosen volumes and masses correspond to a chromium concentration of 1 mmol/l at a ligand to chromium ratio of 1.5 mol/mol, an A/Cr-ratio of 70 mol/mol and a $P(Ph)_4Cl$/Cr-ratio of 1.0 mol/mol.

Following this procedure, a series of trimerization reactions was conducted under variation of pressure and temperature. Furthermore, the modifier $[PPh_4]Cl$ was replaced by tetraethylammoniumchloride-monohydrate $[NEt_4]Cl.H_2O$ (18.5 mg) for a second experimental series.

After the residence time, the reaction in the liquid phase was quenched by transferring the liquid inventory by means of the ethylene pressure to a glass vessel filled with approx. 100 ml water. The mass balance of the experiment was determined via quantification and GC-FID analysis of the gaseous and liquid product separately, followed by comparison with the ethene uptake data.

Based on the measured data, the overall yields and selectivities were determined.

Surprisingly, a very high 1-hexene-yield is observed, with only trace amounts of 1-butene, 1-octene, 1-decene and 1-dodecene. In repetitive experiments under clean and well-defined conditions, no discernible polymer formation was observed. The results are summarized in Table 1.

TABLE 1

Results of ethylene trimerization experiments using the CrCl$_3$(THF)$_3$/PNPNH/TEA/
[PPh$_4$]Cl and [NEt$_4$]Cl•H$_2$O - catalyst system.

| Temp. ° C. | Pressure bar | Residence time min | Modifier/Cr mol/mol | Product g | C4-Yield wt.-% | C6-Yield wt. % | C10-Yield wt.-% | 1-C6 in C6 wt. % |
|---|---|---|---|---|---|---|---|---|
| 80 | 30 | 120 | 0 | 17.0 | 4.8 | 87.2 | 3.6 | 98.0 |
| 65 | 30 | 120 | 0 | 40.4 | 4.5 | 91.1 | 3.3 | 99.4 |
| 80 | 30 | 120 | [PPh$_4$]Cl/Cr = 1 | 36.5 | 4.5 | 88.0 | 1.2 | 97.9 |
| 80 | 50 | 60 | [PPh$_4$]Cl/Cr = 1 | 41.0 | 7.5 | 88.3 | 1.1 | 97.7 |
| 65 | 50 | 90 | [PPh$_4$]Cl/Cr = 1 | 53.7 | 4.8 | 90.3 | 3.0 | 98.5 |
| 65 | 30 | 120 | [PPh$_4$]Cl/Cr = 1 | 42.9 | 4.4 | 90.2 | 3.9 | 98.3 |
| 50[1] | 30 | 120 | [PPh$_4$]Cl/Cr = 1 | 55.4 | 1.7 | 94.0 | 4.0 | 99.4 |
| 80[2] | 50 | 90 | [NEt$_4$]Cl/Cr = 1 | 50.3 | 4.6 | 88.1 | 3.6 | 98.0 |
| 65 | 30 | 90 | [NEt$_4$]Cl/Cr = 1 | 48.9 | 4.3 | 92.0 | 0.2 | 99.2 |
| 80 | 50 | 90 | [NEt$_4$]Cl/Cr = 5 | 42.6 | 5.4 | 88.0 | 3.8 | 98.5 |

[1] ligand/Cr = 1.75, Al/Cr = 25
[2] modifier was added to TEA first

EXAMPLE 2

Ethylene Trimerization with Cr(acac)$_3$/PNPNH/Modifier/TEA

Following the experimental procedure described in example 1, the catalyst was prepared from 72 mg PNPNH-ligand, 0.1 mmol Cr(acac)$_3$, 0.3 mmol of the various halogenide-containing modifiers and 1.3 ml of a 1.9 M-TEA solution in toluene. The catalytic test was then carried out at 50° C. and 30 bar. The results are shown in Table 2 in comparison to an experiment without modifier and CrCl$_3$(THF)$_3$ as chromium source.

Following the experimental procedure described in example 1, the catalyst was prepared from 69 mg PNPNH-ligand, 0.1 mmol Cr(acac)$_3$, 0.3 mmol [N(nBu)$_4$]Cl and 3 ml of a 1.9 M-TEA solution in toluene. The catalytic test was then carried out at 55° C. and 30 bar. The result is shown in FIG. 1 in comparison to a control experiment without the modifier. GC analysis shows that the ethene consumption curve in FIG. 1 can directly be converted into 1-hexene production, since kinetic phase transfer limitations were carefully ruled out and very high C6-selectivities (>92 wt. %) and 1-hexene selectivities within the total C6-fraction beyond 98 wt. % were achieved.

TABLE 2

Results of ethylene trimerization experiments using the Cr(acac)$_3$/PNPNH/TEA/Modifier.

| Temp. ° C. | Pressure bar | Residence time min | Modifier | Product g | C4-Yield wt.-% | C6-Yield wt. % | C10-Yield wt.-% | 1-C6 in C6 wt. % |
|---|---|---|---|---|---|---|---|---|
| 50[1] | 30 | 120 | — | 55.2 | 2.0 | 92.7 | 5.0 | 99.5 |
| 50 | 30 | 40 | [PPh$_4$]Cl | 87.8 | 1.2 | 93.0 | 5.3 | 99.5 |
| 50 | 30 | 40 | [PPh$_4$]Br | 70.4 | 0.9 | 95.0 | 3.6 | 99.6 |
| 50 | 30 | 40 | [PPh$_4$]I | 15.2 | 1.4 | 96.2 | 1.7 | 99.0 |
| 50 | 30 | 60 | [P(n-Bu)$_3$(tetradecyl)]Cl | 86.2 | 1.6 | 92.8 | 5.1 | 99.0 |
| 50 | 30 | 60 | [NPr$_4$]Cl | 58.3 | 2.2 | 91.7 | 5.5 | 99.2 |
| 50 | 30 | 60 | [NEt$_4$]Br | 60.3 | 1.1 | 94.8 | 3.6 | 99.1 |
| 50 | 30 | 60 | [P(n-Bu)$_4$]Br | 56.9 | 1.2 | 93.9 | 4.1 | 99.1 |
| 50 | 30 | 60 | [N(n-Bu)$_4$]Br | 64.5 | 1.2 | 93.8 | 4.0 | 99.1 |

[1] CrCl$_3$(THF)$_3$ as chromium source

EXAMPLE 3

Ethylene Trimerization Using the Cr(acac)$_3$/PNPNH/TEA/[N(nBu)$_4$]Cl-Catalyst System This example shows how the overall performance of the Cr(III)acetylacetonate/PNPNH/TEA-catalyst system can greatly be enhanced by the modifier tetra-n-butylammoniumchloride. The use of Cr(III)acetylacetonate (short Cr(acac)$_3$) is especially attractive due to its availability and low price. Furthermore, this chromium source is readily soluble in toluene, thereby avoiding the need to handle precursor-slurries during catalyst preparation.

EXAMPLE 4

Figure 2:
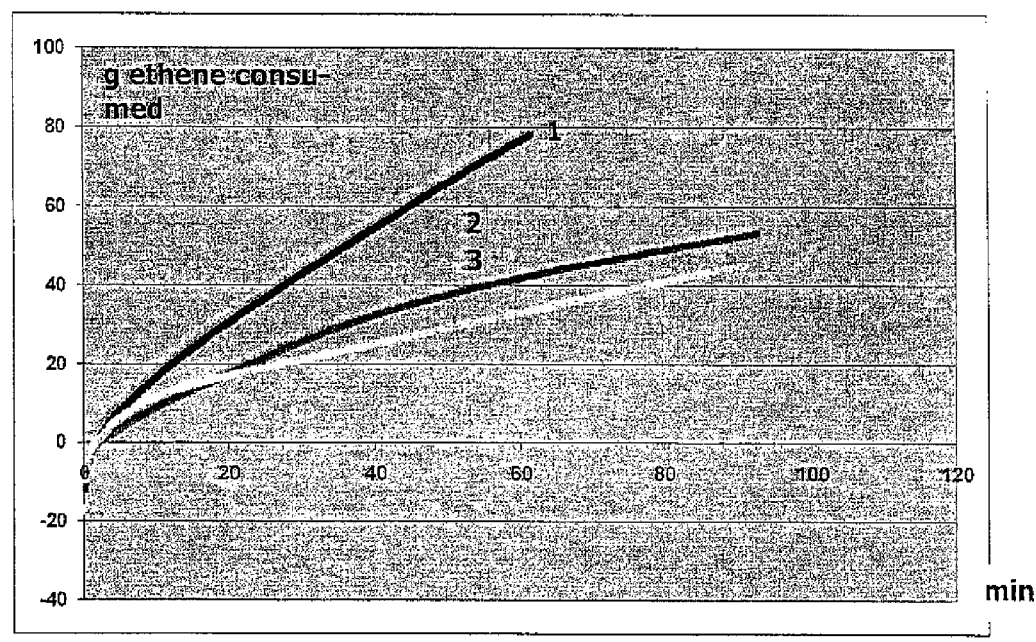

Influence of the Modifiers [H$_3$N(iPr)]Cl, [HN(Et)$_3$]Cl and [N(nBu)$_4$]Cl in Cyclohexane This example shows how 1-hexene can be produced with high activities and selectivities in cyclohexane as solvent, using the modifiers isopropylamine-hydrochloride, triethylamine-hydrochloride and tetra-n-butylammoniumchloride. Again, the catalytic tests were carried out following the experimental procedure of example 1 with the exception that the solvent toluene was replaced by dry cyclohexane. The catalyst was prepared from 69 mg PNPNH-ligand, 0.1 mmol Cr(acac)$_3$, 0.3 mmol of the modifier and 3 ml 1.3 M TEA-solution in heptane. The experimental conditions were chosen as T=55° C. and p=30 bar. GC analysis indicates C6-selectivities >92 wt. % and 1-hexene selectivities within the total C6-fraction beyond 98 wt. %. FIG. 2 shows that the catalytic activity can advantageously be adjusted to desired levels, simply by a suitable choice of the modifier.

EXAMPLE 5

Influence of the Modifier [H$_3$N(iPr)]Cl in Toluene

Figure 3:
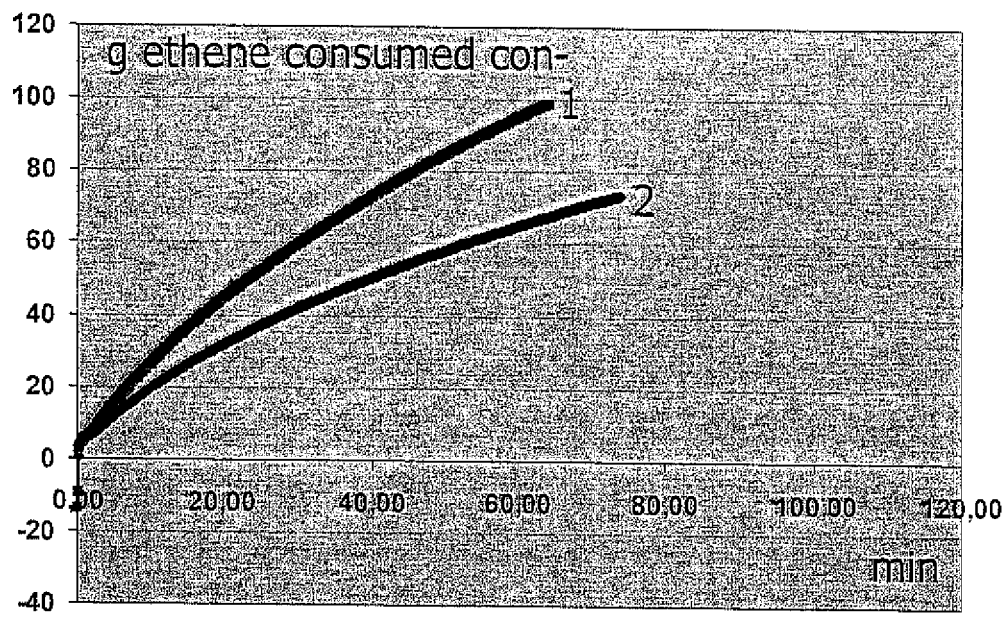

As an alternative to example 4,1-hexene can also be produced with high selectivity by a highly active catalyst in the presence of isopropylamine-hydrochloride, using toluene as solvent. For this experiment, 69 mg of the PNPNH-ligand, 0.1 mmol CrCl$_3$(THF)$_3$, 0.1 mmol [H$_3$N(iPr)]Cl and 1.5 ml of a 1.9 M TEA-solution in toluene were dissolved in 100 ml anhydrous toluene. Directly after mixing the catalyst solution, the reaction was started at 50° C. and 30 bar. For a check of reproducibility and consistency, the experiment was repeated with 0.05 mmol [H$_3$N(iPr)]Cl and constant ligand/ Cr-, TEA/Cr- and modifier/Cr-ratio. FIG. 3 shows that cutting the total catalyst concentration in half leads to an even higher activity with respect to the absolute amount of catalyst used. This is evident by the ethene-uptake curve 2, which shows higher levels than one-half of curve 1.

Again, GC analysis shows clearly that the ethene uptake curve can directly be converted into the 1-hexene product formation curve. C6-selectivities were greater than 92 wt. % in all cases with 1-hexene selectivities in the total C6-fraction beyond 99 wt. %.

EXAMPLE 6

Influence of the Modifier Isopropylamine in Combination with CrCl$_3$(THF)$_3$

Figure 4:
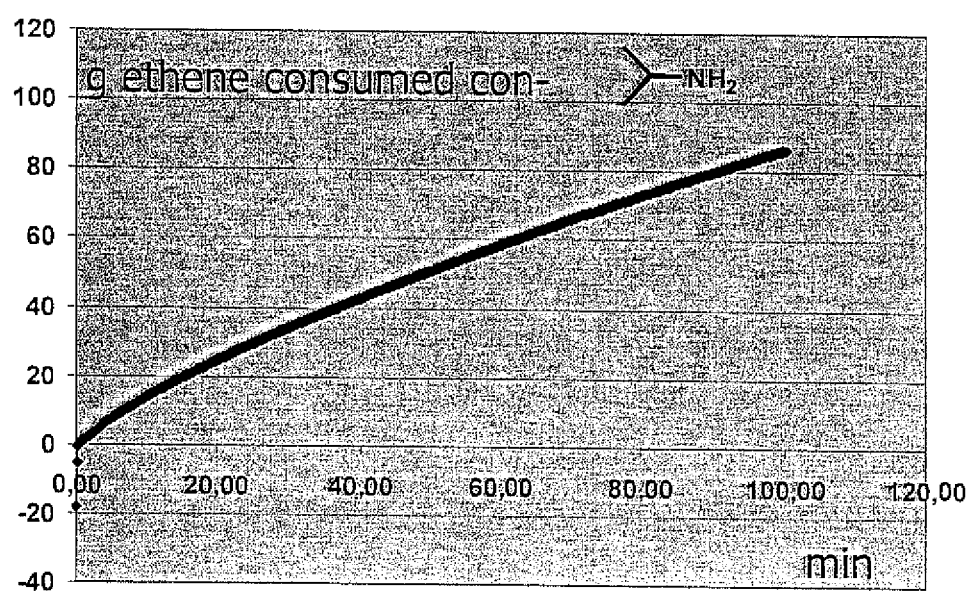

As mentioned before, the advantageous effect of the invention can also be brought about by combining a halide-containing chromium source, such as e.g. CrCl$_3$(THF)$_3$, and a free amine, for instance isopropylamine. For this example, 69 mg of the PNPNH ligand was mixed with 0.1 mmol CrCl$_3$ (THF)$_3$, 0.2 mmol isopropylamine and 1.5 ml 1.9 M TEA in 100 ml anhydrous toluene. The reaction was immediately started at 50° C. (isothermal) and 30 bar ethene pressure. The kinetics of the 1-hexene-formation, indicated by the associated ethene consumption is shown in FIG. 4. GC analysis showed C6-selectivities in excess of 93 wt. % with 1-hexene selectivities in the total C6-fraction beyond 99 wt. %.

EXAMPLE 7

Figure 5:
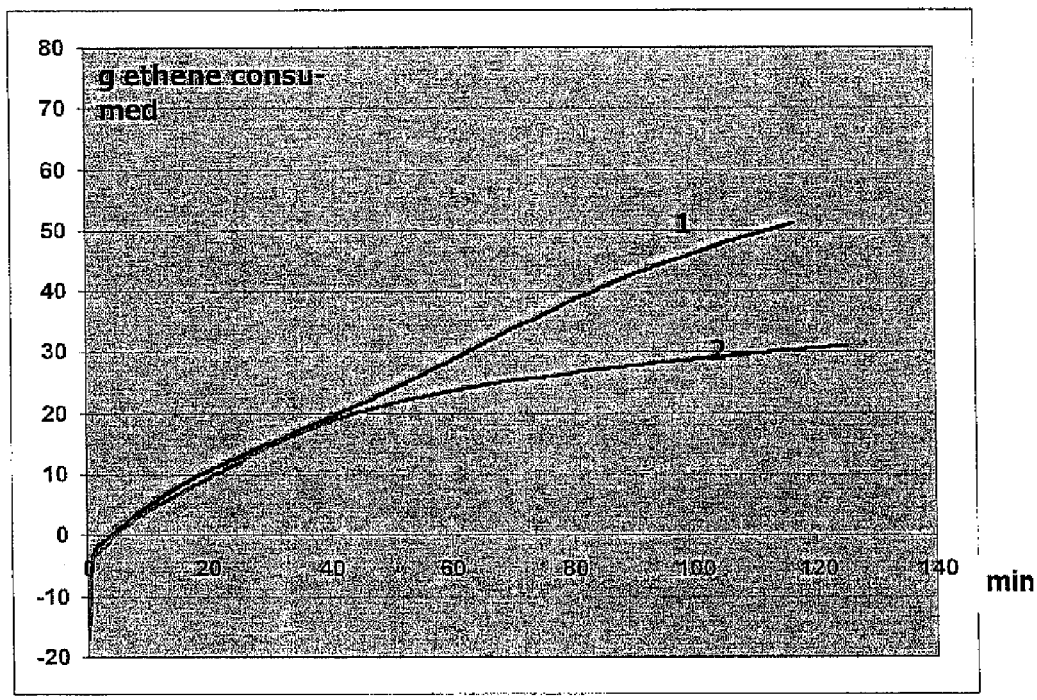

Influence of the Modifier [PPh$_4$]Cl in Combination with the Chromium source Cr(III)acetylacetonate Since Cr(III) acetylacetonate is an especially advantageous chromium source, some efforts have been devoted to catalytic tests using this chromium precursor under various process conditions. For this example, 69 mg PNPNH-ligand was mixed with 0.1 mmol Cr(acac)$_3$, 0.4 mmol [PPh]$_4$Cl, 3 ml 1.9 M TEA solution in toluene and 100 ml anhydrous toluene. The reaction was started as described in the previous examples. Several runs were carried out at various temperatures at an ethene pressure of 30 bar. Exemplary results are shown in FIG. 5 for 70 and 80° C. While the overall activity at 80° C. is somewhat lower than at 70° C., due to partial thermal deactivation, the 1-hexene selectivities remained excellent in both cases. The selectivity figures measured by GC were the same as in the previous examples.

EXAMPLE 8

Figure 6:
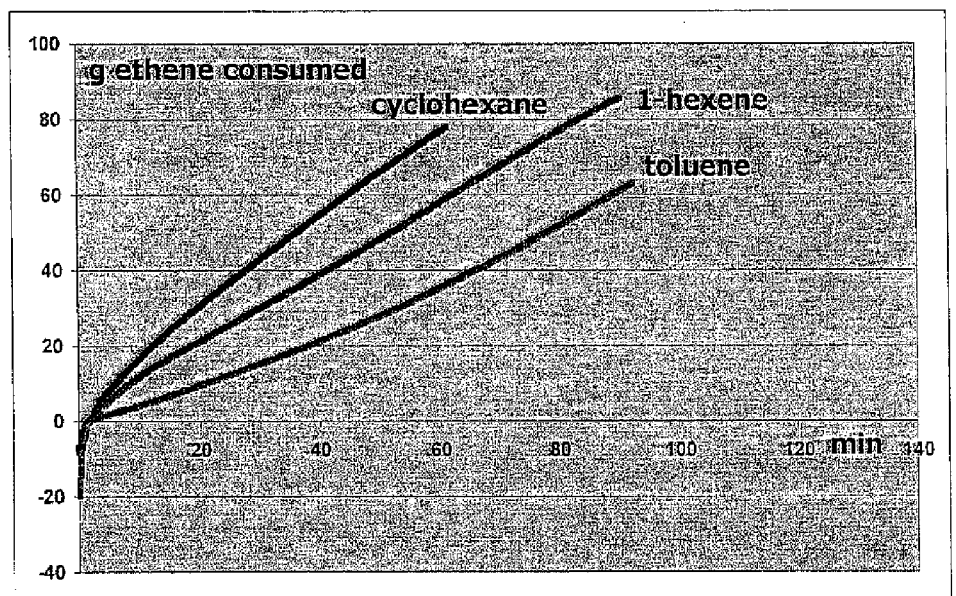

Influence of the Modifier Isopropylammonium-Hydrochloride with Cr(III) Acetylacetonate in Various Solvents: Cyclohexane, 1-Hexene and Toluene This example demonstrates the use of the most preferred solvent 1-hexene. Not only is 1-hexene as a solvent advantageous because it is identical to the product, but it also warrants high activity and selectivity as shown in FIG. 6. 1-Hexene, along with cyclohexane, surpasses even toluene as a solvent. For this experimental series, 69 mg PNPNH-ligand was mixed with 0.1 mmol Cr(acac)$_3$, 0.3 mmol [H$_3$N(iPr)]Cl and 39 mmol TEA in 100 ml of the respective solvent. The temperature was 55° C. and the ethene pressure was chosen as 30 bar. GC analysis showed the same excellent overall 1-hexene selectivities as in the previous examples.

EXAMPLE 9

Influence of the Modifier HCl

Figure 7:
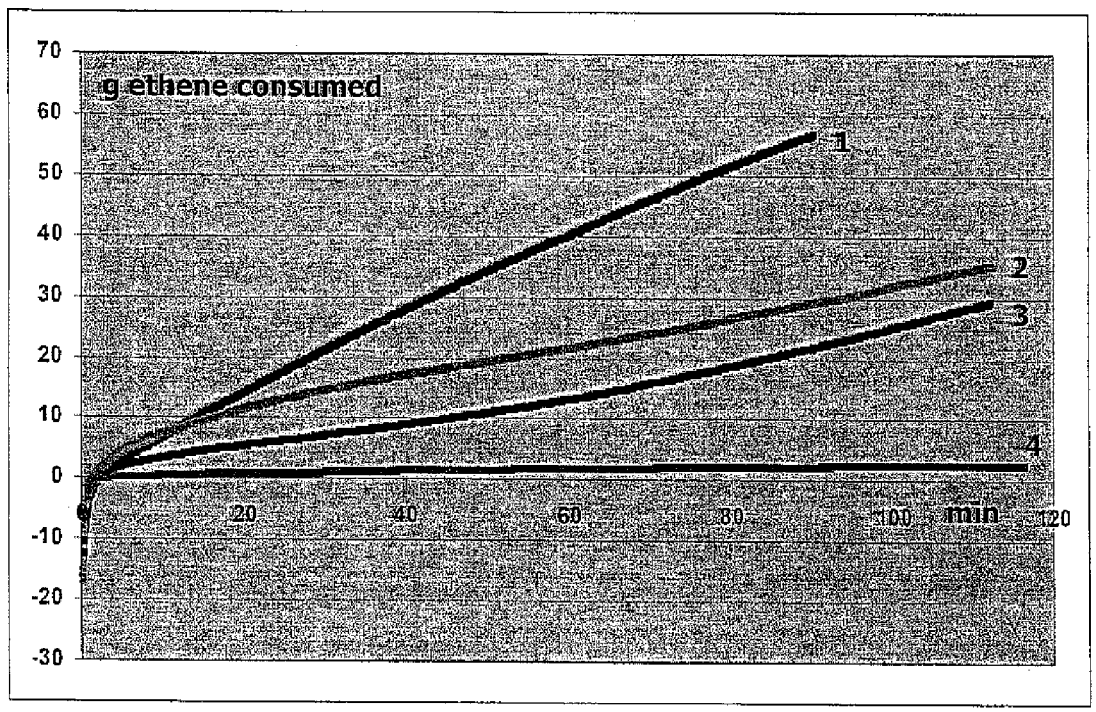

This example demonstrates that, surprisingly, even anhydrous hydrochloric acid is suitable as modifier for the PNPNH-ligand/Cr/TEA-system. In this experimental series, 69 mg PNPNH-ligand, 0.1 mmol Cr(acac)$_3$, 0.3 mmol HCl and 3 ml 1.9 M TEA solution in toluene was mixed with 100 ml anhydrous toluene. The HCl was added as a 1 M solution in diethylether. Reaction conditions were 55° C. and 30 bar. FIG. 7 shows that the activity of this catalyst system depends on the preparation sequence of the catalytic system's constituents but can easily reach the activity figures observed in the previous examples. Also, very high 1-hexene selectivities were obtained, as was the case in examples 1-8.

The features disclosed in the foregoing description, in the claims and in the drawings may, both separately and in any combination thereof, be material for realizing the invention in diverse forms thereof.

The invention claimed is:
1. A catalyst composition comprising:
   (i) a chromium compound;
   (ii) a ligand of the general structure R$_1$R$_2$P—N(R$_3$)—P (R$_4$)—N(R$_5$)—H, wherein R$_1$, R$_2$, R$_3$, R$_4$ and R$_5$ are independently selected from halogen, amino, C$_1$-C$_{10}$-alkyl, substituted C$_1$-C$_{10}$-alkyl, aryl and substituted aryl;
   (iii) a modifier containing organic or inorganic halide; and
   (iv) an activator or co-catalyst.
2. The catalyst composition according to claim 1, wherein the chromium compound is selected from organic or inorganic salts, coordination complexes and organometallic complexes of Cr(II) or Cr(III).
3. The catalyst composition according to claim 2, wherein the modifier is selected from ammonium or phosphonium salts of the type [H$_4$E]X, [H$_3$ER]X, [H$_2$ER$_2$]X, [HER$_3$]X or [ER$_4$]X with E=N or P, X=Cl, Br or I and R=alkyl, cycloalkyl, acyl, aryl, alkenyl, alkynyl or the corresponding bridging di-, tri- or multiunits; HX; or RX.
4. A catalyst composition comprising:
   (i) a halide containing chromium compound
   (ii) a ligand of the general structure R$_1$R$_2$P—N(R$_3$)—P (R$_4$)—N(R$_5$)—H, wherein R$_1$, R$_2$, R$_3$, R$_4$ and R$_5$ are independently selected from C$_1$-C$_{10}$ alkyl, aryl and substituted aryl;
   (iii) a modifier containing a free amine group; and
   (iv) an activator or co-catalyst.

5. The catalyst composition according to claim 4, wherein the modifier contains a free amine group which is a primary, secondary or tertiary aliphatic amine or an aromatic amine.

6. The catalyst composition according to claim 5, wherein the activator or co-catalyst comprises trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane (MAO) or mixtures thereof.

7. The catalyst composition according to claim 6, wherein the molar ligand/Cr ratio is from 0.8:1 to 2.0:1.

8. The catalyst composition according to claim 7, wherein the molar Al/Cr ratio is from 10:1 to 200:1.

9. The catalyst composition according to claim 8, wherein the molar modifier/Cr ratio is from 1:1 to 20:1.

10. The catalyst composition according to any of the preceding claims wherein the molar Cr/halide ratio is from 1:1 to 1:10.

11. A process for the oligomerization of ethylene, comprising contacting ethylene with the catalyst composition of claim 3 under ethylene oligomerization conditions.

12. The process according to claim 11, wherein the chromium compound comprises $CrCl_3(THF)_3$, Cr(III)acetyl acetonate, Cr(III) octanoate, chromium hexacarbonyl, Cr(III)-2-ethylhexanoate, benzene(tricarbonyl)-chromium and Cr(III)chloride.

13. The process according to claim 12, wherein the modifier comprises tetraphenyl phosphonium chloride, tetraethyl ammoniumchloridemonohydrate, tetraethylammoniumchloride, isopropylamine-hydrochloride, triethylamine-hydrochloride, tetrapropylammonium chloride, tetra-n-butylammonium chloride, tetraethylammonium bromide, p-toluidine-hydrochloride, dimethyldistearylammonium chloride, (tri-n-butyl)-n-tetradecylphosphonium chloride, benzoyl chloride or acetyl chloride; the activator or co-catalyst comprises trimethylaluminum, triethyl aluminum, triisopropyl aluminum, triisobutyl aluminum, ethyl aluminum sesquichloride, diethyl aluminum chloride, ethyl aluminum dichloride, methyl aluminoxane (MAO) or mixtures thereof and the oligomerization is carried out at a pressure of 10 to 50 bar and a temperature of from 20 to 100° C.

14. The process according to claim 13 wherein the molar ligand/Cr ratio is from 0.8:1 to 2.0:1, the molar Al/Cr ratio is from 10:1 to 200:1, the molar modifier/Cr ratio is from 1:1 to 20:1, the molar Cr/halide ratio is from 1:1 to 1:10, the activator or co-catalyst comprises trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane (MAO) or mixtures thereof, and the mean residence time of ethylene in the process is from 1 to 4 hours.

15. The catalyst composition of claim 3, wherein the chromium compound comprises $CrCl_3(THF)_3$, Cr(III)acetyl acetonate, Cr(III) octanoate, chromium hexacarbonyl, Cr(III)-2-ethylhexanoate, benzene(tricarbonyl)-chromium or Cr(III)chloride.

16. The catalyst composition of claim 15, wherein the modifier comprises tetraphenyl phosphonium chloride, tetraethyl ammoniumchloride-monohydrate, tetraethylammoniumchloride, isopropylamine-hydrochloride, triethylamine-hydrochloride, tetrapropylammonium chloride, tetra-n-butylammonium chloride, tetraethylammonium bromide, p-toluidine-hydrochloride, dimethyldistearylammonium chloride, (tri-n-butyl)-n-tetradecylphosphonium chloride, benzoyl chloride or acetyl chloride, and the activator or co-catalyst comprises trimethyl aluminum, triethyl aluminum, triisopropyl aluminum, triisobutyl aluminum, ethyl aluminum sesquichloride, diethyl aluminum chloride, ethyl aluminum dichloride, methyl aluminoxane (MAO) or mixtures thereof.

17. The catalyst composition of claim 16, wherein the molar ligand/Cr ratio is from 0.8:1 to 20:1 and the molar Al/Cr ratio is from 10.1 to 200:1.

18. The catalyst composition of claim 17, wherein the molar modifier/Cr ratio is from 1:1 to 20:1 and the molar Cr/halide ratio is from 1:1 to 1:10.

19. The catalyst composition of claim 1, wherein the chromium compound comprises $CrCl_3(THF)_3$ or Cr(III)chloride and the modifier comprises a primary, secondary or tertiary aliphatic amine.

20. The catalyst composition of claim 19, wherein the modifier comprises isopropylamine.

* * * * *